United States Patent [19]

Setoguchi et al.

[11] Patent Number: 5,162,553

[45] Date of Patent: Nov. 10, 1992

[54] PROCESSES FOR PREPARING OPTICALLY ACTIVE 3,4-DIHYDRO-3,4-EPOXY-2H-1-BENZOPYRAN COMPOUNDS AND INTERMEDIATES THEREFOR

[75] Inventors: Shinro Setoguchi; Mineo Tsuruda, both of Fukuoka; Chiaki Kitami, Mie; Tsutomu Yamanaka, Nakatsu, all of Japan

[73] Assignee: Yoshitomi Pharmaceutical Industries, Ltd., Osaka, Japan

[21] Appl. No.: 717,813

[22] Filed: Jun. 19, 1991

Related U.S. Application Data

[62] Division of Ser. No. 486,100, Feb. 28, 1990, Pat. No. 5,066,816.

[30] Foreign Application Priority Data

Mar. 3, 1989 [JP] Japan .................................. 1-52700
May 23, 1989 [JP] Japan .................................. 1-131014

[51] Int. Cl.$^5$ .................. C07D 311/22; C07D 405/12; C07D 409/12
[52] U.S. Cl. .................................. 549/401; 549/345; 549/66; 546/269
[58] Field of Search ......................... 549/60, 345, 401; 546/269

[56] References Cited

U.S. PATENT DOCUMENTS 3,599,200 7/1976 Arnold .
4,062,870 12/1977 Watts .
4,446,113 4/1984 Evans et al. .

FOREIGN PATENT DOCUMENTS 0120428 10/1984 European Pat. Off. .
0273262 7/1988 European Pat. Off. .
0296975 12/1988 European Pat. Off. .
0339562 11/1989 European Pat. Off. .
2204868 11/1988 United Kingdom .

*Primary Examiner*—Nicky Chan
*Attorney, Agent, or Firm*—Wenderoth, Lind & Ponack

[57] ABSTRACT

The present invention provides an industrially valuable method for preparing an optically active 3,4-dihydro-3,4-epoxy-2H-1-benzopyran compound which is useful as a starting material for an optically active benzopyran compound with antihypertensive, coronary blood flow-increasing activities and the like, and also provides a diastereometric ester compound with a 3-halo-4-hydroxy-2H-1-benzopyran compound which is useful as an intermediate for said epoxy compound.

3 Claims, No Drawings

PROCESSES FOR PREPARING OPTICALLY ACTIVE 3,4-DIHYDRO-3,4-EPOXY-2H-1-BENZOPYRAN COMPOUNDS AND INTERMEDIATES THEREFOR

This application is a division of application Ser. No. 486,100, filed Feb. 28, 1990, now U.S. Pat. No. 5,066,816.

FIELD OF THE INVENTION

This invention relates to a process for preparing an optically active 3,4-dihydro-3,4-epoxy-2H-1-benzopyran compound and an intermediate therefor.

BACKGROUND OF THE INVENTION

In U.S. Pat. No. 4,446,113, there is disclosed 6-cyano-3,4-dihydro-2,2-dimethyl-trans-4-(2-oxo-1-pyrrolidinyl)-2H-1-benzopyran 3-ol (BRL-34915). In European Patent Publication No. 273,262, British Patent Publication No. 2,204,868 and European Patent Publication No. 296,975, there are disclosed a group of 4-substituted benzopyran compounds having antihypertensive actions, smooth muscle-relaxant actions and the like.

Moreover, in European Patent Publication No. 339,562, there is disclosed that the novel benzopyran compounds bearing a N-acyl-N-oxy-substituted amino group or hydrazine group at the 4-position, possess hypotensive, coronary blood flow-increasing activities and the like.

Recently, in developing a compound having a chiral carbon atom(s) as drugs, the corresponding optical isomer has become important from the view point of enhancement of the pharmacological activity, removal of the side effect or improvement of the solubility and the like.

The optically active benzopyran compounds having hypotensive or coronary blood flow-increasing activities and the like are disclosed in, for example, European Patent Publication No. 120,428, British Patent Publication No. 2,204,868 and European Patent Publication No. 339,562.

In particular, in British Patent Publication No. 2,204,868, it is disclosed that optically active 3,4-dihydro-3,4-epoxy-2H-1-benzopyran compounds can be obtained by reacting trans-3-bromo-2,2-dimethyl-4-hydroxy-2H-1-benzopyran-6-carbonitrile with (−)-camphanic acid, subjecting the mixture of the obtained diastereomers to silica gel chromatography and then subjecting each of diastereomers to hydrolysis. However, (−)-camphanic acid itself is very expensive, and further, the resolution operation of diastereomers by chromatography consumes a long period of time and a lot of solvents and carriers. In brief, such operation is expensive and complicated, and is not suitable for resolution on a large scale. Though, European Patent Publication No. 339,562 describes that the optically active benzopyran compounds can be produced by employing the optically active starting compounds, no working examples for such starting compounds are illustrated. Therefore, the development of a practically useful method for the resolution has been desired.

SUMMARY OF THE INVENTION

The object of the present invention is to provide a low-cost and convenient process for resolving in a large amount for 3,4-dihydro-3,4-epoxy-2H-1-benzopyran compounds which are useful as an intermediate for drugs.

Another object of the present invention is to provide a diastereomeric ester compound with 3-halo-4-hydroxy-2H-1-benzopyran compound which is useful as an intermediate for said optically active epoxy compound.

DETAILED DESCRIPTION OF THE INVENTION

The present invention relates to a process for preparing an optically active 3,4-dihydro-3,4-epoxy-2H-1-benzopyran compound of the formula (I):

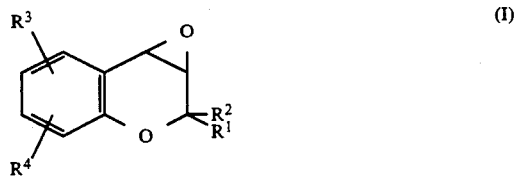

wherein $R^1$ and $R^2$ are the same or different, and each is hydrogen or $C_{1-6}$ alkyl, or $R^1$ and $R^2$ combinedly together form $C_{2-5}$ alkylene, $R^3$ and $R^4$ are the same or different, and each is hydrogen, halogen, nitro, cyano, amino, $C_{1-6}$ alkyl, halo-$C_{1-6}$ alkyl, $C_{1-6}$ alkoxy, carboxy, formyl, $C_{2-6}$ alkanoyl, halo-$C_{2-6}$ alkanoyl, benzoyl, naphthoyl, phenyl-$C_{2-6}$ alkanoyl, naphthyl-$C_{2-6}$ alkanoyl, formylamino, $C_{2-6}$ alkanoylamino, benzoylamino, naphthoylamino, phenyl-$C_{2-6}$ alkanoylamino, naphthyl-$C_{2-6}$ alkanoylamino, carbamoyl, $C_{1-6}$ alkylcarbamoyl, di-$C_{1-6}$ alkylcarbamoyl, $C_{1-6}$ alkylsulfinyl, phenylsulfinyl, naphthylsulfinyl, $C_{1-6}$ alkylsulfonyl, phenylsulfonyl, naphthylsulfonyl, sulfamoyl, $C_{1-6}$ alkylsulfamoyl or di-$C_{1-6}$ alkylsulfamoyl, in which the term "phenyl", "naphthyl", "benzoyl", and "naphthoyl" include substituted phenyl, substituted naphthyl, substituted benzoyl and substituted naphthoyl by at least one substituent selected from the group consisting of halogen, hydroxy, amino, nitro, cyano, $C_{1-6}$ alkyl, $C_{1-6}$ alkoxy and trifluoromethyl on the ring.

Further, the present invention relates to a compound of the formula (II):

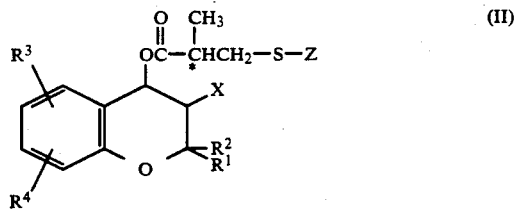

wherein Z is hydrogen, —CO—$C_{1-6}$ alkyl or —CO—Ar, where Ar is phenyl, naphthyl, thienyl, furyl, pyridyl, or substituted phenyl, naphthyl, thienyl, furyl or pyridyl by 1 to 3 substituents selected from the group consisting of halogen, amino, nitro, hydroxy, $C_{1-6}$ alkyl or $C_{1-6}$ alkoxy, X is bromine, chlorine or iodine and other symbols are as defined above and the asterisked carbon atom has (S)-(−)- or (R)-(+)- configuration.

As the preferable compounds of formula (II), the compounds of formula (II) wherein X is bromine are exemplified.

The methods of the present invention comprise (i) reacting a compound of the formula (III):

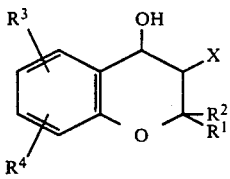 (III)

wherein each symbol is as defined above, with a compound of the formula (IV):

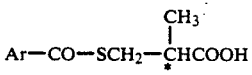 (IV)

wherein Ar is phenyl, naphthyl, thienyl, furyl, pyridyl, or substituted phenyl, naphthyl, thienyl, furyl or pyridyl said groups being substituted by 1 to 3 substituents selected from the group consisting of halogen, amino, nitro, hydroxy, $C_{1-6}$ alkyl or $C_{1-6}$ alkoxy and the asterisked carbon atom has (S)-(−)- or (R)-(+)- configuration, or the corresponding reactive derivative on the carboxyl group, or (ii) reacting a compound of the formula (II-a):

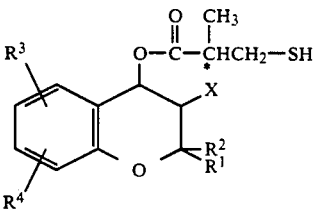 (II-a)

wherein each symbol is as defined above, with a compound of the formula (V):

 (V)

wherein Ar is as defined above or the corresponding reactive derivative on the carboxyl group, subjecting a compound of the formula (II-b):

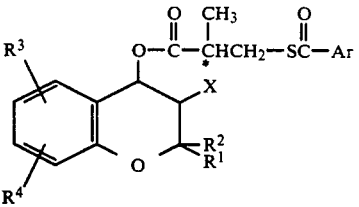 (II-b)

wherein each symbol is as defined above, thus obtained by the steps (i) or (ii) to fractional crystallization, and hydrolysis followed by cyclizing.

The compounds of formula (II-a) and (II-b) correspond to the compounds of formula (II) wherein Z is hydrogen or —CO—Ar, respectively.

In the above-mentioned definitions, halogen means fluorine, chlorine, bromine and iodine; $C_{1-6}$ alkyl means methyl, ethyl, propyl, isopropyl, butyl, isobutyl, tert-butyl, pentyl, isopentyl, hexyl and the like; halo-$C_{1-6}$ alkyl means chloromethyl, bromomethyl, fluoromethyl, iodomethyl, dichloromethyl, dibromomethyl, difluoromethyl, diiodomethyl, trifluoromethyl, chloroethyl, bromoethyl, fluoroethyl, iodoethyl, difluoroethyl, trifluoroethyl, chloropropyl, bromopropyl, fluoropropyl, iodopropyl, difluoropropyl, trifluoropropyl, chlorobutyl, bromobutyl, fluorobutyl, iodobutyl, difluorobutyl, trifluorobutyl and the like; $C_{2-5}$ alkylene means ethylene, trimethylene, propylene, tetramethylene, pentamethylene and the like; $C_{1-6}$ alkoxy means methoxy, ethoxy, propoxy, isopropoxy, butoxy, isobutoxy, tert-butoxy, pentyloxy, hexyloxy and the like; $C_{2-6}$ alkanoyl means acetyl, propionyl, butyryl, valeryl, pivaloyl, hexanoyl and the like; halo-$C_{2-6}$ alkanoyl means chloroacetyl, bromoacetyl, fluoroacetyl, iodoacetyl, dichloroacetyl, dibromoacetyl, difluoroacetyl, diiodoacetyl, trifluoroacetyl, chloropropionyl, bromopropionyl, fluoropropionyl, iodopropionyl, difluoropropionyl, trifluoropropionyl, chlorobutyryl, bromobutyryl, fluorobutyryl, iodobutyryl, difluorobutyryl, trifluorobutyryl, fluorovaleryl, fluorohexanoyl and the like; phenyl-$C_{2-6}$ alkanoyl means phenylacetyl, phenylpropionyl, phenylbutyryl, phenylvaleryl, phenylhexanoyl and the like; naphthyl-$C_{2-6}$ alkanoyl means naphthylacetyl, naphthylpropionyl, naphthylbutyryl, naphthylvaleryl, naphthylhexanoyl and the like; $C_{2-6}$ alkanoylamino means acetylamino, propionylamino, butyrylamino, isobutyrylamino, valerylamino, pivaloylamino, hexanoylamino and the like; phenyl-$C_{2-6}$ alkanoylamino means phenylacetylamino, phenylpropionylamino, phenylbutyrylamino, phenylvalerylamino, phenylhexanoylamino and the like; naphthyl-$C_{2-6}$ alkanoylamino means naphthylacetylamino, naphthylpropionylamino, naphthylbutyrylamino, naphthylvalerylamino, naphthylhexanoylamino and the like; $C_{1-6}$ alkylcarbamoyl means methylcarbamoyl, ethylcarbamoyl, propylcarbamoyl, isopropylcarbamoyl, butylcarbamoyl, isobutylcarbamoyl, tert-butylcarbamoyl, pentylcarbamoyl, hexylcarbamoyl and the like; di-$C_{1-6}$ alkylcarbamoyl means dimethylcarbamoyl, diethylcarbamoyl, dipropylcarbamoyl, diisopropylcarbamoyl, dibutylcarbamoyl, diisobutylcarbamoyl, di-tert-butylcarbamoyl, dipentylcarbamoyl, dihexylcarbamoyl, N-methyl-N-ethylcarbamoyl, N-methyl-N-propylcarbamoyl, N-methyl-N-butylcarbamoyl, N-methyl-N-tert-butylcarbamoyl, N-methyl-N-pentylcarbamoyl, N-methyl-N-hexylcarbamoyl and the like; $C_{1-6}$ alkylsulfinyl means methylsulfinyl, ethylsulfinyl, propylsulfinyl, isopropylsulfinyl, butylsulfinyl, isobutylsulfinyl, tert-butylsulfinyl, pentylsulfinyl, hexylsulfinyl and the like; $C_{1-6}$ alkylsulfonyl means methylsulfonyl, ethylsulfonyl, propylsulfonyl, isopropylsulfonyl, butylsulfonyl, isobutylsulfonyl, tert-butylsulfonyl, pentylsulfonyl, hexylsulfonyl and the like, $C_{1-6}$ alkylsulfamoyl means methylsulfamoyl, ethylsulfamoyl, propylsulfamoyl, isopropylsulfamoyl, butylsulfamoyl, isobutylsulfamoyl, tert-butylsulfamoyl, pentylsulfamoyl, hexylsulfamoyl and the like; di-$C_{1-6}$ alkylsulfamoyl means dimethylsulfamoyl, diethylsulfamoyl, dipropylsulfamoyl, diisopropylsulfamoyl, dibutylsulfamoyl, diisobutylsulfamoyl, di-tert-butylsulfamoyl, dipentylsulfamoyl, dihexylsulfamoyl, N-methyl-N-ethylsulfamoyl, N-methyl N-propylsulfamoyl, N-methyl-N-isopropylsulfamoyl, N-methyl-N-butylsulfamoyl, N-methyl-N-isobutylsulfamoyl, N-methyl-N-tert-butylsulfamoyl, N-methyl-N-pentylsulfamoyl, N-methyl-N hexylsulfamoyl and the like; naphthyl means 1-naphthyl and 2-naphthyl; thienyl means 2-thienyl and 3-thienyl; furyl means 2-furyl and 3-furyl; pyridyl means 2-pyridyl, 3-pyridyl and 4-pyridyl.

The process of the present invention will be explained in more detail,

First, the compounds of formula (II) can be prepared by the following methods:

Method 1

The compounds of formula (II-b) can be prepared by reacting a compound of the formula (III) with a chiral carboxylic acid of the formula (IV) and the reactive derivatives thereof (e.g. acid halide, acid anhydride).

The reaction is carried out at room temperature and under heating, if necessary, under cooling, in the absence or, preferably presence of an acid scavenger in a suitable solvent. The solvents include benzene, toluene, chloroform, methylene chloride, ethylene chloride, ether and so on. The acid scavengers include pyridine, triethylamine, potassium carbonate and so on.

Method 2

The compounds of formula (II-b) can also be prepared by reacting a compound of the formula (II-a) with a carboxylic acid of the formula (V) and a reactive derivative thereof e.g. acid halide, acid anhydride).

In this method, the compound of the formula (II-a) can be prepared by reacting a compound of the formula (III) with a compound of the formula (VI):

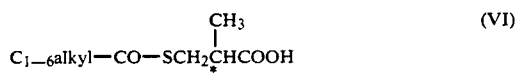

and the reactive derivatives (e.g. acid halide, acid anhydride) in a similar manner as described in Method 1 and further subjecting the obtained compound of formula (II-c):

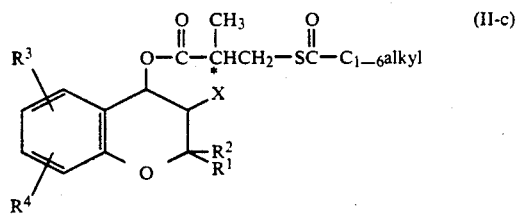

wherein each symbol is as defined above, to hydrolysis under a mild condition in the presence of a base.

The compounds of formula (II-c) correspond to the compounds of formula (II) wherein Z is —CO—$C_{1-6}$ alkyl.

The bases employed include hydrazine hydrate, methylhydrazine, triethylamine, sodium hydroxide, potassium hydroxide, potassium carbonate and so on. The preferable compound of formula (VI) is an optically active 2-acetylthiomethylpropionic acid.

The following compounds can be illustrated as the compounds of formula (II) obtained in the above-mentioned manner.

(1) (±)-Trans-3-bromo-6-cyano-3,4-dihydro-2,2-dimethyl-4-[(S)-(−)-3-(3,5-dinitrobenzoylthio)-2-methylpropionyloxy]-2H-1-benzopyran
(2) (±)-Trans-3-bromo-6-cyano-3,4-dihydro-2,2-dimethyl-4-[(S)-(−)-3 (3,4-dichlorobenzoylthio)-2-methylpropionyloxy]-2H-1-benzopyran
(3) (±)-Trans-3-bromo-6-cyano-3,4-dihydro-2,2-dimethyl-4-[(S)-(−)-3-(3,5-dichlorobenzoylthio)-2-methylpropionyloxy]-2H-1-benzopyran
(4) (±)-Trans-3-bromo-6-cyano-3,4-dihydro-2,2-dimethyl-4-[(S)-(−)-3-(4-bromobenzoylthio)-2-methylpropionyloxy]-2H-1-benzopyran
(5) (±)-Trans-3-bromo-6-cyano-3,4-dihydro-2,2-dimethyl-4-[(S)-(−)-3-benzoylthio)-2-methylpropionyloxy]-2H-1-benzopyran
(6) (±)-Trans-3-bromo-6-cyano-3,4-dihydro-2,2-dimethyl-4-[(S)-(−)-3-(2-methylbenzoylthio)-2-methylpropionyloxy]-2H-1-benzopyran
(7) (±)-Trans-3-bromo-6-cyano-3,4-dihydro-2,2-dimethyl-4-[(S)-(−)-3-(4-methoxybenzoylthio)-2-methylpropionyloxy]-2H-1-benzopyran
(8) (±)-Trans-3-bromo-6-nitro-3,4-dihydro-2,2-dimethyl-4-[(S)-(−)-3-(4-fluorobenzoylthio)-2-methylpropionyloxy]-2H-1-benzopyran
(9) (±)-Trans-3-bromo-6-nitro-3,4-dihydro-2,2-dimethyl-4-[(S)-(−)-3-(3,5-dinitrobenzoylthio)-2-methylpropionyloxy]-2H-1-benzopyran
(10) (±)-Trans-3-bromo-3,4-dihydro-2,2-dimethyl-4-[(S)-(−)-3-(4-methylbenzoylthio)-2-methylpropionyloxy]-2H-1-benzopyran
(11) (±)-Trans-3-bromo-6-phenylsulfonyl-3,4-dihydro-2,2-dimethyl-4-[(S)-(−)-3-(α-naphthoylthio)-2-methylpropionyloxy]-2H-1-benzopyran
(12) (±)-Trans-7-amino-3-bromo-3,4-dihydro-2,2-dimethyl-6-nitro-4-[(S)-(−) 3-(3,5-dinitrobenzoylthio)-2-methylpropionyloxy]-2H-1-benzopyran
(13) (±)-Trans-7-amino-3-bromo-3,4-dihydro-2,2-dimethyl-6-nitro-4-[(R)-(+)-3-(3,5-dinitrobenzoylthio)-2-methylpropionyloxy]-2H-1-benzopyran
(14) (±)-Trans-7-acetylamino-3-bromo-3,4-dihydro-2,2-dimethyl-6 -nitro-4-[(S)-(−)-3-(3,5-dinitrobenzoylthio)-2-methylpropionyloxy]-2H-1-benzopyran
(15) (±)-Trans-7-acetylamino-3-bromo-3,4-dihydro-2,2-dimethyl-6-nitro-4-[(R)-(+)-3-(3,5-dinitrobenzoylthio)-2-methylpropionyloxy]-2H-1-benzopyran Since one of the diastereomer mixtures of formula (II) obtained by Methods 1 and 2 can be crystallized by a conventional fractional crystallization, two kinds of diastereomers can be easily separated, and then each of the diastereomers is subjected to hydrolysis to obtain the optically active compounds of formula (I).

The solvents for fractional crystallization include, for example, an ester of acetic acid such as methyl acetate, ethyl acetate or butyl acetate, an alcohol such as methanol, ethanol or propanol, a halogenated hydrocarbon such as methylene chloride, chloroform or ethylene chloride, an aromatic hydrocarbon such as benzene, toluene or xylene, an ether such as diethyl ether, diisopropyl ether, tetrahydrofuran or dioxane or water, dimethylformamide, dimethylacetamide or acetone and a mixture of these two or more solvents.

The hydrolysis can be carried out by a conventional manner and any known means under the condition that epimerization does not occur, can be applied. Preferably, the hydrolysis reaction can be carried out at a temperature from room temperature to a temperature below the boiling point of a solvent employed in the presence of an alkali metal salt such as sodium hydroxide, potassium hydroxide, sodium carbonate or potassium carbonate. The solvent includes water, methanol, ethanol, dioxane and so on or a mixed solvent thereof. Moreover, the said reaction can be carried out under an acidic condition, for example, by using hydrochloric acid, sulfuric acid or hydrobromic acid.

The following compounds can be illustrated as the optically active compound of formula (I) as prepared in the above-mentioned manner.

(1) (+)-6-Cyano-3,4-dihydro-3,4-epoxy-2,2-dimethyl-2H-1-benzopyran
(2) (−)-6-Cyano-3,4-dihydro-3,4-epoxy-2,2-dimethyl-2H-1-benzopyran
(3) (+)-3,4-Dihydro-3,4-epoxy-2,2-dimethyl-2H-1-benzopyran
(4) (−)-3,4-Dihydro-3,4-epoxy-2,2-dimethyl-2H-1-benzopyran
(5) (+)-3,4-Dihydro-3,4-epoxy-6-nitro-2,2-dimethyl-2H-1-benzopyran
(6) (−)-3,4-Dihydro-3,4-epoxy-6-nitro-2,2-dimethyl-2H-1-benzopyran
(7) (+)-3,4-Dihydro-3,4-epoxy-6-phenylsulfonyl-2,2-dimethyl-2H-1-benzopyran
(8) (−)-3,4-Dihydro-3,4-epoxy-6-phenylsulfonyl-2,2-dimethyl-2H-1-benzopyran
(9) (+)-3,4-Dihydro-3,4-epoxy-6-acetylamino-2,2-dimethyl-2H-1-benzopyran
(10) (−)-3,4-Dihydro-3,4-epoxy-6-acetylamino-2,2-dimethyl-2H-1-benzopyran
(11) (+)-3,4-Dihydro-3,4-epoxy-2,2,N,N-tetramethyl-2H-1-benzopyran-6-carboxamide
(12) (−)-3,4-Dihydro-3,4-epoxy-2,2,N,N-tetramethyl-2H-1-benzopyran-6-carboxamide
(13) (+)-7-Amino-3,4-dihydro-3,4-epoxy-6-nitro-2,2-dimethyl-2H-1-benzopyran
(14) (−)-7-Amino-3,4-dihydro-3,4-epoxy-6-nitro-2,2-dimethyl-2H-1-benzopyran
(15) (+)-7-Acetylamino-3,4-dihydro-3,4-epoxy-6-nitro-2,2-dimethyl-2H-1-benzopyran
(16) (−)-7-Acetylamino-3,4-dihydro-3,4-epoxy-6-nitro-2,2-dimethyl-2H-1-benzopyran According to the methods of the present invention, only one of the diastereomers can be crystallized, when diastereomeric mixture of the ester compounds of formula (II-b) produced by using the optically active acid compound of formula (IV) or by way of the compounds of formula (II-a) was dissolved in the solvent. Therefore, it is not necessary to employ the additional separation steps such as column chromatography and the objective compounds can be easily and simply separated by means of fractional crystallization. Further, since the compounds of formulae (IV), (V) and (VI) are easily available, the methods of the present invention have extremely industrial values. Moreover, the objective compounds of formula (I) obtained by the methods of the present invention, can be used as intermediates leading to the optically active benzopyran compounds which are disclosed, for example, in European Patent Publication No. 339,562, and exhibit remarkably long-lasting hypotensive actions and the like.

For instance, (+)-trans-4-(N-acetyl-N-benzyloxy)amino-6-cyano-3,4-dihydro-2,2-dimethyl-2H-1-benzopyran-3-ol, melting at 145–147° C. (hereinafter referred to as compound A), as a novel benzopyran compound can be produced by reacting (−)-6-cyano-3,4-dihydro-2,2-dimethyl-3,4-epoxy-2H-1-benzopyran with O-benzylhydroxylamine and further, reacting the obtained (+)-trans-4-(N-benzyloxy)amino-6-cyano-3,4-dihydro-2,2-dimethyl-2H-1-benzopyran-3-ol with acetyl chloride.

The present invention will be concretely explained by the following examples, but they are not construed to limit to the scope of the invention.

EXAMPLE 1

To a mixture of 14.5 g of (±)-trans-3-bromo-6-cyano-3,4-dihydro-2,2-dimethyl-4-hydroxy-2H-1-benzopyran, 60 ml of ethylene chloride and 1.6 ml of pyridine was added 5.5 g of (S)-(−)-3-(3,5-dinitrobenzoylthio)-2-methylpropionyl chloride under ice-cooling and was stirred for 1.5 hours under room temperature. The reaction mixture was washed with diluted hydrochloric acid once and 10% aqueous sodium chloride solution twice. The organic layer was separated, dried over magnesium sulfate and concentrated under reduced pressure to give 8.9 g of (±)-trans-3-bromo-6-cyano-3,4-dihydro-2,2-dimethyl-4-[(S)-(−)-3-(3,5-dinitrobenzoylthio)-2-methylpropionyloxy]-2H-1-benzopyran as light yellow semicrystals.

EXAMPLE 2

(1) To a mixture of 94 g of (±)-trans-3-bromo-6-cyano-3,4-dihydro-2,2-dimethyl-4-hydroxy-2H-1-benzopyran, 800 ml of ethylene chloride and 32.4 ml of pyridine was added 66 g of (S)-(−)-3-acetylthio-2-methylpropionyl chloride under ice-cooling over 5 minutes and stirred for 1.5 hours under room temperature. The reaction mixture was washed with diluted hydrochloric acid once and 10% aqueous sodium chloride solution twice. The organic layer was separated, dried over magnesium sulfate and concentrated under reduced pressure to give 139.8 g of (±)-trans-3-bromo-6-cyano-3,4-dihydro-2,2-dimethyl-4-[(S)-(−)-3-acetylthio-2-methylpropionyloxy]-2H-1-benzopyran as a light yellow oily substance.

(2) To a solution of 139.8 g of (±)-trans-3-bromo-6-cyano-3,4-dihydro-2,2-dimethyl-4-[(S)-(−)-3-acetylthio-2-methylpropionyloxy]-2H-1-benzopyran dissolved in 1 l of ethanol was added 20 g of hydrazine monohydrate under ice-cooling and stirred for 1.5 hours. To the reaction mixture was added 3 l of water and extracted with chloroform. After separating, the organic layer was washed with diluted hydrochloric acid once and 10% aqueous sodium chloride solution once, dried over magnesium sulfate and then concentrated under reduced pressure. To a mixture of 126.9 g of the residue, 800 ml of ethylene chloride and 32 ml of pyridine was added 79 g of 3,5-dinitrobenzoyl chloride under ice cooling over 5 minutes and stirred for 1.5 hours under room temperature. The resulting solution was washed with diluted hydrochloric acid once and 10% aqueous sodium chloride solution once, dried over magnesium sulfate and then concentrated under reduced pressure to give 175.7 g of (±)-trans-3-bromo-6-cyano-3,4-dihydro-2,2-dimethyl-4-[(S)-(−)-3-(3,5-dinitrobenzoylthio)-2-methylpropionyloxy]-2H-1-benzopyran as light yellow semicrystals.

EXAMPLE 3

(±)-Trans-3-bromo-6-cyano-3,4-dihydro-2,2-dimethyl-4-[(S)-(−)-3-(3,5-dinitrobenzoylthio)-2-methylpropionyloxy]-2H-1-benzopyran (113 g) was dissolved in 600 ml of ethyl acetate under heating and then cooled. The precipitated crystals were collected by filtration and dried to give 46.35 g of the corresponding (−) form as slightly yellow crystals, melting at 181–183° C. Optical rotation:$[\alpha]_D^{23} = -27.4°$ (c=1, chloroform)

The filtrate was concentrated and to the residue was added 2 l of methanol and heated to dissolve. Upon cooling the precipitated crystals were collected by filtration and dried to give 41.6 g of the corresponding (+) form as slightly yellow crystals, melting at 125–127° C. Optical rotation: $[\alpha]_D^{23} = +54.37°$ (c=1, chloroform).

The purities of both diastereomers are more than 99% by NMR (nuclear magnetic spectrum).

EXAMPLE 4

To a solution of 38.4 g of (−) form crystals obtained in Example 3 dissolved in 380 ml of dioxane was added dropwise 115 ml of 3N sodium hydroxide at room temperature over 10 minutes and stirred at 40° C. for 50 minutes. After cooling, to the reaction mixture was added 2 l of water and extracted with ethyl acetate. The organic layer was washed with saturated aqueous sodium chloride solution once, collected by fractionation and dried over magnesium sulfate. After concentrating under reduced pressure, the residue was crystallized from ethyl acetate to give 9.2 g of (+)-6-cyano-3,4-dihydro-3,4-epoxy-2,2-dimethyl-2H-1-benzopyran as white crystals, melting at 138–143° C. Optical rotation:- $[\alpha]_D^{23} = +88.59°$ (c=1, methylene chloride).

EXAMPLE 5

To a solution of 36 g (+) form crystals obtained in Example 3 dissolved in 360 ml of dioxane was added dropwise 108 ml of 3N sodium hydroxide at room temperature over 10 minutes and stirred at 40–50° C. for 2 hours. After cooling, to the reaction mixture was added for 2 l of water and extracted with ethyl acetate. The organic layer was washed with saturated aqueous sodium chloride solution twice, separated, and dried over magnesium sulfate and then concentrated under reduced pressure. The residue was crystallized from ethyl acetate to give 7.7 g of (−)-6-cyano-3,4-dihydro-3,4-epoxy-2,2-dimethyl-2H-1-benzopyran as white crystals, melting at 140–143° C. Optical rotation:- $[\alpha]_D^{23} = -86.07°$ (c=1, methylene chloride).

EXAMPLE 6

(1) To a mixture of (±)-trans-7-acetylamino-3-bromo-4-hydroxy-3,4-dihydro-6-nitro-2,2-dimethyl-2H-1-benzopyran, ethylene chloride and pyridine was added (S)-(−)-3-acetylthio-2-methylpropionyl chloride under ice-cooling over 5 minutes and stirred for 1.5 hours under room temperature. The reaction mixture was washed with diluted hydrochloric acid once and 10% aqueous sodium chloride solution twice. The organic layer was separated, dried over magnesium sulfate and concentrated under reduced pressure to give (±)-trans-7-acetylamino-3-bromo-3,4-dihydro-6-nitro-2,2-dimethyl-4-[(S)-(−)-3-acetylthio-2-methylpropionyloxy]-2H-1-benzopyran.

(2) To a solution of (±)-trans-7-acetylamino-3-bromo-3,4-dihydro-6-nitro-2,2-dimethyl-4-[(S)-(−)-3-acetylthio-2-methylpropionyloxy]-2H-1-benzopyran dissolved in 1 l of ethanol was added hydrazine monohydrate under ice-cooling and stirred for 1.5 hours. To the reaction mixture was added 3 l of water and extracted with chloroform. After separating, the organic layer was washed with diluted hydrochloric acid once and 10% aqueous sodium chloride solution once, dried over magnesium sulfate and then concentrated under reduced pressure. To a mixture of the residue, ethylene chloride and pyridine was added 3,5-dinitrobenzoyl chloride under ice-cooling over 5 minutes and stirred for 1.5 hours under room temperature. The resulting solution was washed with diluted hydrochloric acid once and 10% aqueous sodium chloride solution once, dried over magnesium sulfate and then concentrated under reduced pressure to give (±)-trans-7-acetylamino-3-bromo-3,4-dihydro-6-nitro-2,2-dimethyl-4-[(S)-(−)-3-(3,5-dinitrobenzoylthio)-2-methylpropionyloxy]-2H-1-benzopyran.

EXAMPLE 7

(±)-Trans-7-acetylamino-3-bromo-3,4-dihydro-6-nitro-2,2-dimethyl-4-[(S)-(−)-3-(3,5-dinitrobenzoylthio)-2-methylpropionyloxy]-2H-1-benzopyran was dissolved in ethyl acetate under heating and then cooled. The precipitated crystals were collected by filtration and dried to give the corresponding (−) form.

The filtrate was concentrated and to the residue was added 2 l of methanol and heated to dissolve. Upon cooling the pricipitated crystals were collected by filtration and dried to give the corresponding (+) form.

The purities of both diastereomers are more than 99% by NMR (nuclear magnetic spectrum).

EXAMPLE 8

To a solution of (−) form crystals obtained in Example 7 dissolved in dioxane was added dropwise 3N sodium hydroxide at room temperature over 10 minutes and stirred at 40° C. for 50 minutes. After cooling, to the reaction mixture was added 2 l of water and extracted with ethyl acetate. The organic layer was washed with saturated aqueous sodium chloride solution once, collected by fractionation and dried over magnesium sulfate. After concentrating under reduced pressure, the residue was crystallized from ethyl acetate to give (+)-7-amino-6-nitro-3,4-dihydro-3,4-epoxy-2,2-dimethyl-2H-1-benzopyran.

EXAMPLE 9

To a solution of (+) form crystals obtained in Example 7 dissolved in dioxane was added dropwise 3N sodium hydroxide at room temperature over 10 minutes and stirred at 40–50° C. for 2 hours. After cooling, to the reaction mixture was added for 2 l of water and extracted with ethyl acetate. The organic layer was washed with saturated aqueous sodium chloride solution twice, separated, and dried over magnesium sulfate and then concentrated under reduced pressure. The residue was crystallized from ethyl acetate to give (−)-7-amino-6-nitro-3,4-dihydro-3,4-epoxy-2,2-dimethyl-2H-1-benzopyran.

The following compounds can be prepared in a similar manner mentioned in Examples 1, 2, 3, 6 or 7.

(1) (±)-Trans-3-bromo-6-cyano-3,4-dihydro-2,2-dimethyl-4-[(S)-(−)-3-(3,4-dichlorobenzoylthio)-2-methylpropionyloxy]-2H-1-benzopyran (2) (±)-Trans-3-bromo-6-cyano-3,4-dihydro-2,2-dimethyl-4-[(S)-(−)-3-(3,5-dichlorobenzoylthio)-2-methylpropionyloxy]-2H-1-benzopyran (3) (±)-Trans-3-bromo-6-cyano-3,4-dihydro-2,2-dimethyl-4-[(S)-(−)-3-(4-bromobenzoylthio)-2-methylpropionyloxy]-2H-1-benzopyran (4) (±)-Trans-3-bromo-6-cyano-3,4-dihydro-2,2-dimethyl-4-[(S)-(−)-3-benzoylthio-2-methylpropionyloxy]-2H-1-benzopyran (5) (±)-Trans-3-bromo-6-cyano-3,4-dihydro-2,2-dimethyl-4-[(S)-(−)-3-(2-methylbenzoylthio)-2-methylpropionyloxy]-2H-1-benzopyran (6) (±)-Trans-3-bromo-6-cyano-3,4-dihydro-2,2-dimethyl-4-[(S)-(−)-3-(4-methoxybenzoylthio)-2-methylpropionyloxy]-2H-1-benzopyran (7) (±)-Trans-3-bromo-6-nitro-3,4-dihydro-2,2-dimethyl-4-[(S)-(−)-3-(4-fluorobenzoylthio)-2-methylpropionyloxy]-2H-1-benzopyran (8) (±)-Trans-3-bromo-6-nitro-3,4-dihydro-2,2-dimethyl-4-[(S)-(−)-3-(3,5-dinitrobenzoylthio)-2-methylpropionyloxy]-2H-1-benzopyran (9) (+)-Trans-3-bromo-6-nitro-3,4-dihydro-2,2-dimethyl-4-[(S)-(−)-3-(3,5-dinitrobenzoylthio)-2-methylpropionyloxy]-2H-1-benzopyran, melting at 148–150° C., Optical rotation: $[\alpha]_D^{23} = +51.0°$ (c=1, methylene chloride)

(10) (−)-Trans-3-bromo-6-nitro-3,4-dihydro-2,2-dimethyl-4-[(S)-(−)-3-(3,5-dinitrobenzoylthio)-2-methylpropionyloxy]-2H-1-benzopyran, melting at 165–168° C., Optical rotation: $[\alpha]_D^{23} = -40.2°$ (c=1, methylene chloride)

(11) (±)-Trans-3-bromo-3,4-dihydro-2,2-dimethyl-4-[(S)-(−)-3-(4-methylbenzoylthio)-2-methylpropionyloxy]-2H-1-benzopyran

(12) (+)-Trans-3-bromo-6-phenylsulfonyl-3,4-dihydro-2,2-dimethyl-4-[(S)-(−)-3-(α-naphthoylthio)-2-methylpropionyloxy]-2H-1-benzopyran

(13) (+)-Trans-7-amino-3-bromo-3,4-dihydro-6-nitro-2,2-dimethyl-4-[(S)-(−)-3-(3,5-dinitrobenzoylthio)-2-methylpropionyloxy]-2H-1-benzopyran

(14) (−)-Trans-7-amino-3-bromo-3,4-dihydro-6-nitro-2,2-dimethyl-4-[(S)-(−)-3-(3,5-dinitrobenzoylthio)-2-methylpropionyloxy]-2H-1-benzopyran Further, the following compounds can be prepared in a similar manner mentioned in Examples 4, 5, 8 or 9.

(15) (+)-3,4-Dihydro-3,4-epoxy-2,2-dimethyl-2H-1-benzopyran

(16) (−)-3,4-Dihydro-3,4-epoxy-2,2-dimethyl-2H-1-benzopyran

(17) (+)-3,4-Dihydro-3,4-epoxy-6-nitro-2,2-dimethyl-2H-1-benzopyran, melting at 85–87° C., Optical rotation: $[\alpha]_D^{24} = +165.4°$ (c=1, methylene chloride)

(18) (−)-3,4-Dihydro-3,4-epoxy-6-nitro-2,2-dimethyl-2H-1-benzopyran, melting at 86–88° C., Optical rotation: $[\alpha]_D^{25} = -162.6°$ (c=1, methylene chloride)

(19) (+)-3,4-Dihydro-3,4-epoxy-6-phenylsulfonyl-2,2-dimethyl-2H-1-benzopyran

(20) (−)-3,4-Dihydro-3,4-epoxy-6-phenylsulfonyl-2,2-dimethyl-2H-1-benzopyran

(21) (+)-6-acetylamino-3,4-dihydro-3,4-epoxy-2,2-dimethyl-2H-1-benzopyran

(22) (−)-6-acetylamino-3,4-dihydro-3,4-epoxy-2,2-dimethyl-2H-1-benzopyran

(23) (+)-3,4-Dihydro-3,4-epoxy-2,2,N,N-tetramethyl-2H-1-benzopyran-6-carboxamide

(24) (−)-3,4-Dihydro-3,4-epoxy-2,2,N,N-tetramethyl-2H-1-benzopyran-6-carboxamide

(25) (+)-7-Acetylamino-3,4-epoxy-3,4-dihydro-2,2-dimethyl-6-nitro-2H-1-benzopyran

(26) (−)-7-Acetylamino-3,4-epoxy-3,4-dihydro-2,2-dimethyl-6-nitro-2H-1-benzopyran Although the present invention has been adequately discussed in the foregoing specification and examples included therein, one readily recognizes that various changes and modifications may be made without departing from the spirit and scope thereof.

What is claimed is:

1. A compound of the formula (I):

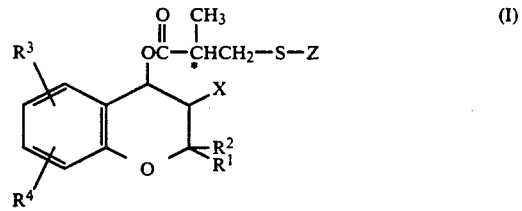

wherein $R^1$ and $R^2$ are the same or different, and each is hydrogen or $C_{1-6}$ alkyl, or $R^1$ and $R^2$ combinedly together form $C_{2-5}$ alkylene, $R^3$ and $R^4$ are the same or different, and each is hydrogen, halogen, nitro, cyano, amino, $C_{1-6}$ alkyl, halo-$C_{1-6}$ alkyl, $C_{1-6}$ alkoxy, carboxy, formyl, $C_{2-6}$ alkanoyl, halo-$C_{2-6}$ alkanoyl, benzoyl, naphthoyl, phenyl-$C_{2-6}$ alkanoyl, naphthyl-$C_{2-6}$ alkanoyl, formylamino, $C_{2-6}$ alkanoylamino, benzoylamino, naphthoylamino, phenyl-$C_{2-6}$ alkanoylamino, naphthyl-$C_{2-6}$ alkanoylamino, carbamoyl, $C_{1-6}$ alkylcarbamoyl, di-$C_{1-6}$ alkylcarbamoyl, $C_{1-6}$ alkylsulfinyl, phenylsulfinyl, naphthylsulfinyl, $C_{1-6}$ alkylsulfonyl, phenylsulfonyl, naphthylsulfonyl, sulfamoyl, $C_{1-6}$ alkylsulfamoyl or di-$C_{1-6}$ alkylsulfamoyl, in which the terms "phenyl", "naphthyl", "benzoyl" and "naphthoyl" include substituted phenyl, substituted naphthyl, substituted benzoyl and substituted naphthoyl, the substituents being at least one substituent selected from the group consisting of halogen, hydroxy, amino, nitro, cyano, $C_{1-6}$ alkyl, $C_{1-6}$ alkoxy and trifluoromethyl on the ring, Z is hydrogen, —CO— $C_{1-6}$ alkyl or —CO—Ar, where Ar is phenyl, naphthyl, thienyl, furyl, pyridyl, or substituted phenyl, naphthyl, thienyl, furyl, pyridyl by 1 to 3 substituents selected from the group consisting of halogen, amino, nitro, hydroxy, $C_{1-6}$ alkyl or $C_{1-6}$ alkoxy, X is bromine, chlorine or iodine and the asterisked carbon atom has (S)-(−)- or (R)-(+)- configuration.

2. A compound of claim 1 wherein X is bromine.

3. A compound according to claim 2, said compound being (+)-trans-3-bromo-6-cyano-3,4-dihydro-2,2-dimethyl-4-[(S)-(−)-3-(3,5-dinitrobenzoylthio)-2-methylpropionyloxy]-2H-1-benzopyran.

* * * * *